US007200534B2

(12) United States Patent
Heumann et al.

(10) Patent No.: US 7,200,534 B2
(45) Date of Patent: Apr. 3, 2007

(54) RADIOGRAPHIC IMAGING SYSTEMS AND METHODS FOR DESIGNING SAME

(75) Inventors: John M. Heumann, Loveland, CO (US); Gerald L. Meyer, Fort Collins, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/074,122

(22) Filed: Mar. 7, 2005

(65) Prior Publication Data

US 2006/0200326 A1 Sep. 7, 2006

(51) Int. Cl.
*G06G 7/48* (2006.01)
(52) U.S. Cl. .................. 703/4; 703/3; 703/5; 703/6; 703/2; 378/1; 378/119; 378/145
(58) Field of Classification Search ................ 600/391; 378/4–157; 703/1, 3–6; 430/5–320
See application file for complete search history.

(56) References Cited

U.S. PATENT DOCUMENTS

| 4,383,327 | A |   | 5/1983  | Kruger              |
|-----------|---|---|---------|---------------------|
| 4,926,452 | A |   | 5/1990  | Baket et al.        |
| 5,398,684 | A | * | 3/1995  | Hardy ........ 600/391 |
| 5,583,904 | A |   | 12/1996 | Adams               |
| 5,808,962 | A | * | 9/1998  | Steinberg et al. ...... 367/7 |
| 5,867,553 | A | * | 2/1999  | Gordon et al. ......... 378/4 |
| 6,324,249 | B1|   | 11/2001 | Fazzio              |
| 6,760,399 | B2| * | 7/2004  | Malamud ......... 378/9 |
| 6,990,171 | B2| * | 1/2006  | Toth et al. ........ 378/16 |
| 2003/0108146 | A1 | * | 6/2003 | Malamud ........ 378/19 |
| 2004/0184576 | A1 |   | 9/2004 | Meyer              |
| 2004/0236550 | A1 | * | 11/2004 | Edic et al. ....... 703/2 |
| 2004/0251419 | A1 | * | 12/2004 | Nelson et al. ..... 250/370.09 |

OTHER PUBLICATIONS

Computer Tomography, Principles, Design, Artifacts, and Recent Advances, J. Hsich, SPIE Press, 2003.*
"Principles of Digital Radiography with Large-Area Electronically Readable Detectors: A Review of the Basics", Chotas et al, RSNA, Duke University, 1999.*
"Design and application of a multi-modal process tomography system", Hoyle et al, IOP Publishing, 2001.*

(Continued)

*Primary Examiner*—Fred Ferris

(57) ABSTRACT

In one embodiment, a method for designing a radiographic imaging system includes 1) receiving a number of design constraints for the system, and then 2) in response to the constraints, generating a plurality of radiographic imaging system designs, each having a different number of radiographic sources, and each requiring a different number of nominal scan passes to image a specimen region of interest. Designs having a greater number of radiographic sources have sets of translated radiographic detection areas sharing at least some coincident, nominal scan passes as compared to radiographic imaging system designs having fewer radiographic sources. Each set of translated radiographic detection areas is associated with a radiographic source that is replicated and translated with respect to a radiographic source that forms part of a radiographic imaging system design having fewer radiographic sources. Related systems and apparatus are also disclosed.

7 Claims, 10 Drawing Sheets

OTHER PUBLICATIONS

"Principles of Computerized Tomographic Imaging", Kak et al, IEEE press, 1999.*

"X-ray detectorys for digital radiography", Yaffe et al, IOP Publishing 1997.*

"Electrical capacitance tomography for flow imaging: system model for development of image reconstruction algorithms and design of primary sensors", Xie et al, IEE Proceedings, vol. 139, No. 1, Feb. 1992.*

"Physically realistic Monte Carlo simulation of source, collimator and tomographic data acquisition for emission computer tomography", Yanch et al, Phys. Med. Niol., 1992, vol. 37, No. 4, 853-870.*

Stephen F. Scheiber, "X-ray's 2-D vs. 3-D debate: To slice or not to slice?", www.tmworld.com, at least as early as Sep. 21, 2004, 4 pages.

* cited by examiner

RADIOGRAPHIC IMAGING SYSTEMS AND METHODS FOR DESIGNING SAME

BACKGROUND

Radiographic imaging systems are variously described, for example, in U.S. Pat. No. 4,383,327 of Kruger, U.S. Pat. No. 5,583,904 of Adams, U.S. Pat. No. 6,324,249 B1 of Fazzio, and published U.S. patent application Ser. No. 20040184576 A1 of Meyer. Kruger describes a scanning radiographic system employing a multi-linear array of radiographic sensors operated in a time delay and integration mode. Adams describes a laminography system that allows generation of high speed and high resolution x-ray laminographs using a continuous scan method, two or more linear detectors, and one or more collimated x-ray sources. Fazzio describes a linear scanning geometry laminography system that allows for generation of high speed and high resolution x-ray laminographs using an electronic detector operated in a time-domain integration mode, coupled with a moving source of x-rays. Meyer discloses an x-ray inspection system using a single x-ray source and a planar array of linear sensors that are aligned with their long axes in parallel. In contrast to Adams, in which an article to be inspected makes a single pass over a column of linear sensors, Meyer teaches that an article to be inspected makes a plurality of passes over an array of linear sensors.

Some radiographic imaging systems (e.g., that disclosed by Kruger) are two-dimensional, which means that the relationship between a radiographic source, one or more radiographic detectors, and a specimen to be imaged, enables the imaging of a single plane of the specimen. Other radiographic imaging systems are three-dimensional (e.g., those disclosed by Adams, Fazzio and Meyer), which means that the relationship between the system's radiographic sources, radiographic detectors, and a specimen to be imaged, enables the imaging of multiple planes or a three-dimensional region of the specimen. A three-dimensional imaging system can also enable the construction of a three-dimensional model of the specimen. As a result, three-dimensional systems are often better suited to the inspection of complex or multi-layered specimens, or specimens having features of interest that are obscured by other features.

SUMMARY OF THE INVENTION

In one embodiment, a radiographic imaging system comprises an imaging system having plural radiographic sources and an array of radiographic detection areas. Different sets of the radiographic detection areas sense radiation transmitted by different ones of the radiographic sources. Each relationship between a given one of the radiographic sources and a given one of the radiographic detection areas that senses its radiation corresponds to a relationship between a radiographic source and radiographic detection area in a multiple scan pass, single source imaging system model. Relationships between the sets of radiographic detection areas correspond to translations of the radiographic detection areas in the imaging system model. The system further comprises an image acquisition system that operates the imaging system as a specimen to be imaged moves relative to the imaging system in a plurality of scan passes. The system also comprises a motion control system to vary relative positions of the imaging system and specimen to thereby provide the plurality of scan passes. At least some of the scan passes cause radiation from at least two of the radiographic sources to be 1) transmitted through a specimen region of interest, and 2) detected by radiographic detection areas belonging to at least two corresponding sets of radiographic detection areas.

In another embodiment, a radiographic imaging system comprises an imaging system having plural radiographic sources and an array of radiographic detection areas. The radiographic sources and radiographic detection areas are fixed with respect to one another, and different sets of the radiographic detection areas sense radiation transmitted by different ones of the radiographic sources. The system further comprises an image acquisition system that operates the imaging system as a specimen to be imaged moves relative to the imaging system in a plurality of scan passes. The system also comprises a motion control system to vary relative positions of the imaging system and specimen to thereby provide the plurality of scan passes. At least some of the scan passes cause radiation from at least two of the radiographic sources to be 1) transmitted through a specimen region of interest, and 2) detected by radiographic detection areas belonging to at least two corresponding sets of radiographic detection areas.

In another embodiment, a method for designing a radiographic imaging system comprises 1) receiving a number of design constraints for the radiographic imaging system, and then 2) in response to the constraints, generating a plurality of radiographic imaging system designs, each having a different number of radiographic sources, and each requiring a different number of nominal scan passes to image a specimen region of interest. The designs having a greater number of radiographic sources comprise sets of translated radiographic detection areas sharing at least some coincident, nominal scan passes as compared to radiographic imaging system designs having fewer radiographic sources. Each set of translated radiographic detectors is associated with a radiographic source that is replicated and translated with respect to a radiographic source that forms part of a radiographic imaging system design having fewer radiographic sources.

In yet another embodiment, a scalable radiographic imaging system platform comprises a specimen holder, an imaging system, and a motion control system. The imaging system has a first one or more structures to hold a plurality of radiographic sources, and a second one or more structures to hold a plurality of radiographic detectors. The structures hold each radiographic source and its corresponding radiographic detectors on opposite sides of the specimen holder, in fixed positions with respect to one another. The platform also comprises a motion control system to vary relative positions of the imaging system and specimen holder, in accordance with a scan pass pattern dictated by the numbers and positions of radiographic sources and radiographic detectors installed in the structures of the imaging system.

Other embodiments are also disclosed.

BRIEF DESCRIPTION OF THE DRAWINGS

Illustrative embodiments of the invention are illustrated in the drawings, in which.

DETAILED DESCRIPTION OF AN EMBODIMENT

U.S. Pat. No. 5,583,904 of Adams discloses an x-ray inspection system employing a single column of linear sensors, different ones of which are irradiated by different x-ray sources. Each of the x-ray sources irradiates its corresponding sensors at different angles, thereby enabling each of the sensors to acquire a different image or projection of a specimen to be imaged. One advantage of Adams' system is its high throughput. That is, Adams' system can image a specimen in only a single scan pass across its sensors. However, to do so requires the use of multiple x-ray sources, which increases system cost.

In contrast to Adams' system, published U.S. patent application Ser. No. 20040184576 A1 of Meyer discloses an x-ray inspection system employing a single x-ray source and an array of linear sensors. Each of the sensors acquires a different image or projection of a specimen to be imaged. However, for each sensor to acquire a complete image of the specimen, the specimen must make multiple scan passes across the sensors.

The inventors have realized that the systems disclosed by Adams and Meyers are related by a number of design variables, such as system image quality (including, but not limited to, the choice of how many images or projections of a specimen to acquire, and the elevation and azimuth angles of the projections), system cost, and system throughput. If some but not all of these design variables are constrained, a plurality of different radiographic imaging system designs (i.e., a family of system designs) may be developed. For example, if one specifies system constraints of "fourteen projections at given elevation angles", then cost and throughput may be varied from high-to-low to generate a plurality of system designs, each having different numbers of radiographic sources (thereby providing system cost variations), and each requiring a different number of scan passes to image a specimen region of interest (thereby providing system throughput variations). By generating these system designs, a manufacturer or user could be presented with a plurality of system designs from which one could be selected based on previously unspecified design variables (e.g., cost and throughput in the above example).

Figure 1:
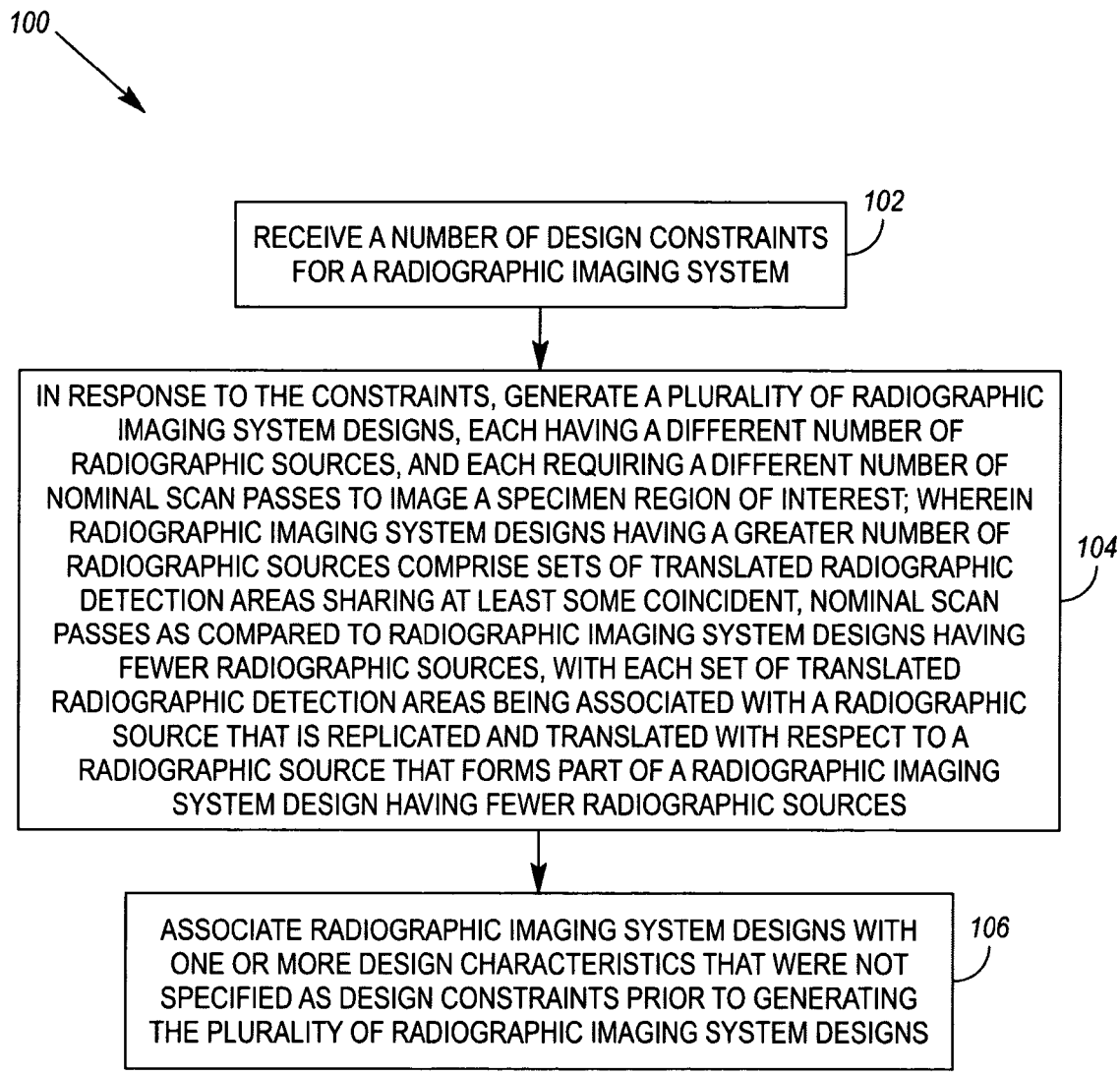
FIG. 1 illustrates an exemplary method for designing a radiographic imaging system.

In light of the above realization, FIG. 1 illustrates an exemplary method 100 for designing a radiographic imaging system. The method 100 commences with the receipt 102 of a number of design constraints for the radiographic imaging system. As previously mentioned, these constraints may include a predetermined system image quality, a system cost, a system throughput or other factors.

In response to the received constraints, the method 100 then proceeds with the generation 104 of a plurality of radiographic imaging system designs that are consistent with the above constraint(s), but differing in their numbers of radiographic sources and nominal scan passes that are required to image a specimen region of interest (ROI).

Figure 2:
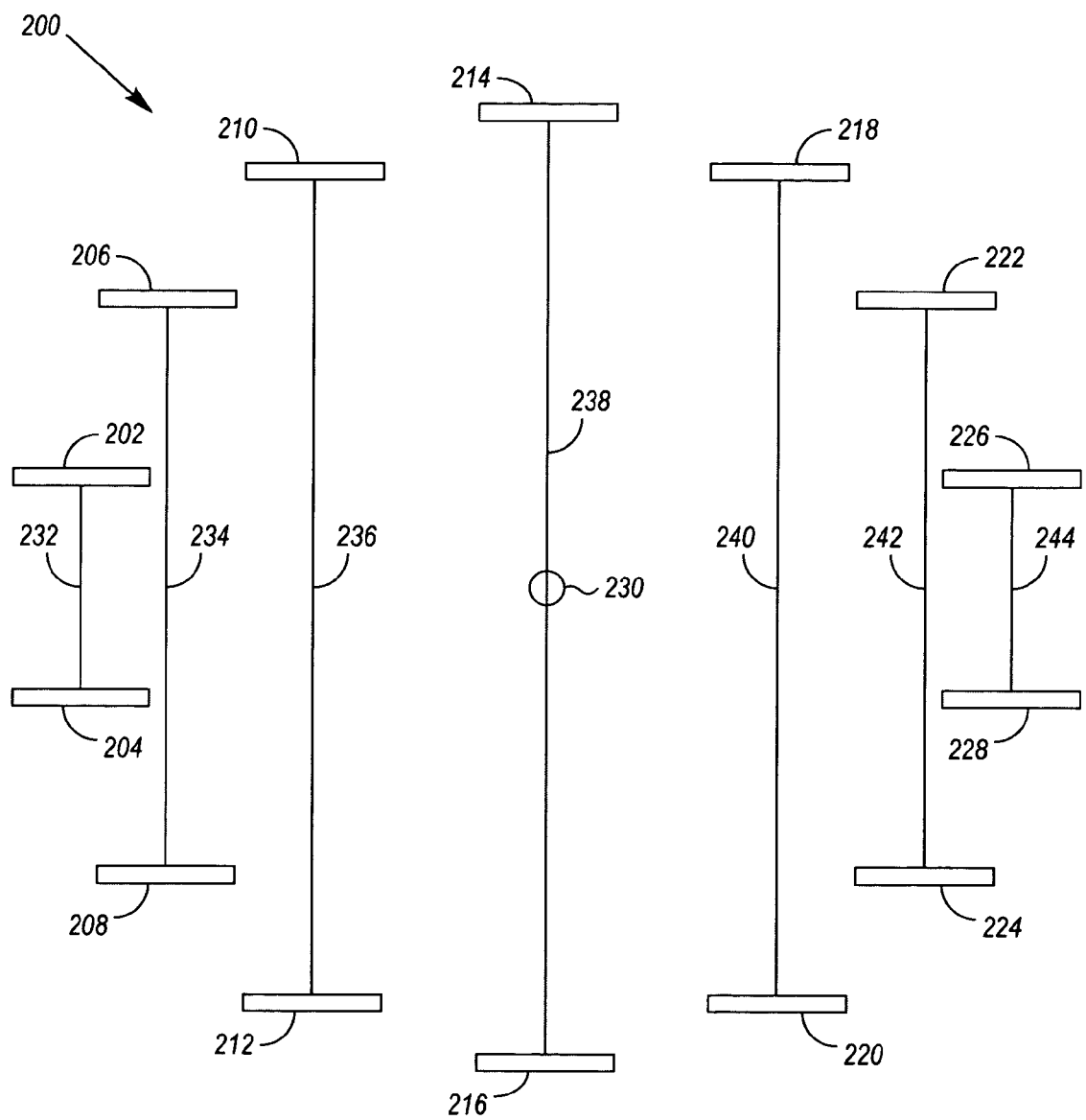
FIG. 2 illustrates a radiographic imaging system design comprising linear detectors spaced at equal azimuth angles.

As defined herein, a "nominal scan path" is a path followed by a reference point within a specimen region of interest (ROI) as the ROI moves in relation to a system's radiographic source and detector sets. In the exemplary step-and-repeat scanning systems that will be presented in this description, a nominal scan path will typically comprise one or more nominal scan passes, as illustrated by the line segments 232–244 shown in FIG. 2. FIG. 2 can be imagined as illustrating a number of nominal scan passes traversed by the reference point superimposed on a minified image of a detector array, or equivalently, a magnified image of the nominal scan passes superimposed on an actual detector array.

As will be described in greater detail later in this description, system designs (e.g., system 700) having a greater number of radiographic sources may comprise sets of translated radiographic detection areas (e.g., linear detection areas) sharing at least some coincident, nominal scan passes as compared to system designs (e.g., system 300) having fewer radiographic sources. In system designs having sets of translated radiographic detection areas, each set of translated radiographic detection areas is associated with a radiographic source that is replicated and translated with respect to a radiographic source that forms part of a radiographic imaging system design having fewer radiographic sources.

Optionally, the method 100 may include associating 106 each design with one or more design characteristics that were not specified as design constraints prior to generating the plurality of system designs. In this manner, a manufacturer or user may make an informed decision on which design fulfills a particular need. As will be described later, the designs may also be used to construct a scalable radiographic imaging system platform, in which radiographic sources and detectors may be added, removed or repositioned to alternately implement various ones of a family of radiographic imaging system designs.

FIGS. 3 & 7–10 illustrate plan views of one exemplary family of system designs that could be generated via the method 100. Although each design is shown flattened, actual implementations of the designs would require suspending their radiographic sources above or below a plane (or planes) in which the radiographic detectors are arranged. See, for example, FIG. 4, which illustrates an elevation of the design 300 shown in FIG. 3 (note that, in FIG. 4, the radiographic detectors 202–216 hide the radiographic detectors 218–228).

The system designs shown in FIGS. 3 & 7–10 may be generated in a variety of ways, one of which will now be described in detail. To begin, a number of (i.e., one or more) system design constraints are received. In this example, the constraints relate to system image quality and consist of specifying the acquisition of fourteen projections, each taken at a fixed elevation angle but different azimuth angle. Experiments have indicated that digital tomography based on fourteen projections, each taken at a fixed elevation angle and approximately equally spaced azimuth angle, can provide cross-sectional images of typical solder joints that are comparable in quality to those provided by the 5DX Automated X-ray Inspection System offered by Agilent Technologies, Inc. (a Delaware corporation headquartered in Palo Alto, Calif., USA).

Given the image quality constraints of fourteen projections, a radiographic imaging system design 200 employing only one radiographic source may be laid out as shown in FIG. 2. The system 200 shown in FIG. 2 may be considered "optimized for image quality" in that it positions each of its fourteen radiographic detectors 202–228 at approximately equally spaced azimuth angles with respect to the system's single radiographic source 230. The lines 232, 234, 236, 238, 240, 242, 244 through the centers of the detector pairs 202/204, 206/208, 210/212, 214/216, 218/220, 222/224 are indicative of nominal scan passes 232–244.

Figure 3:
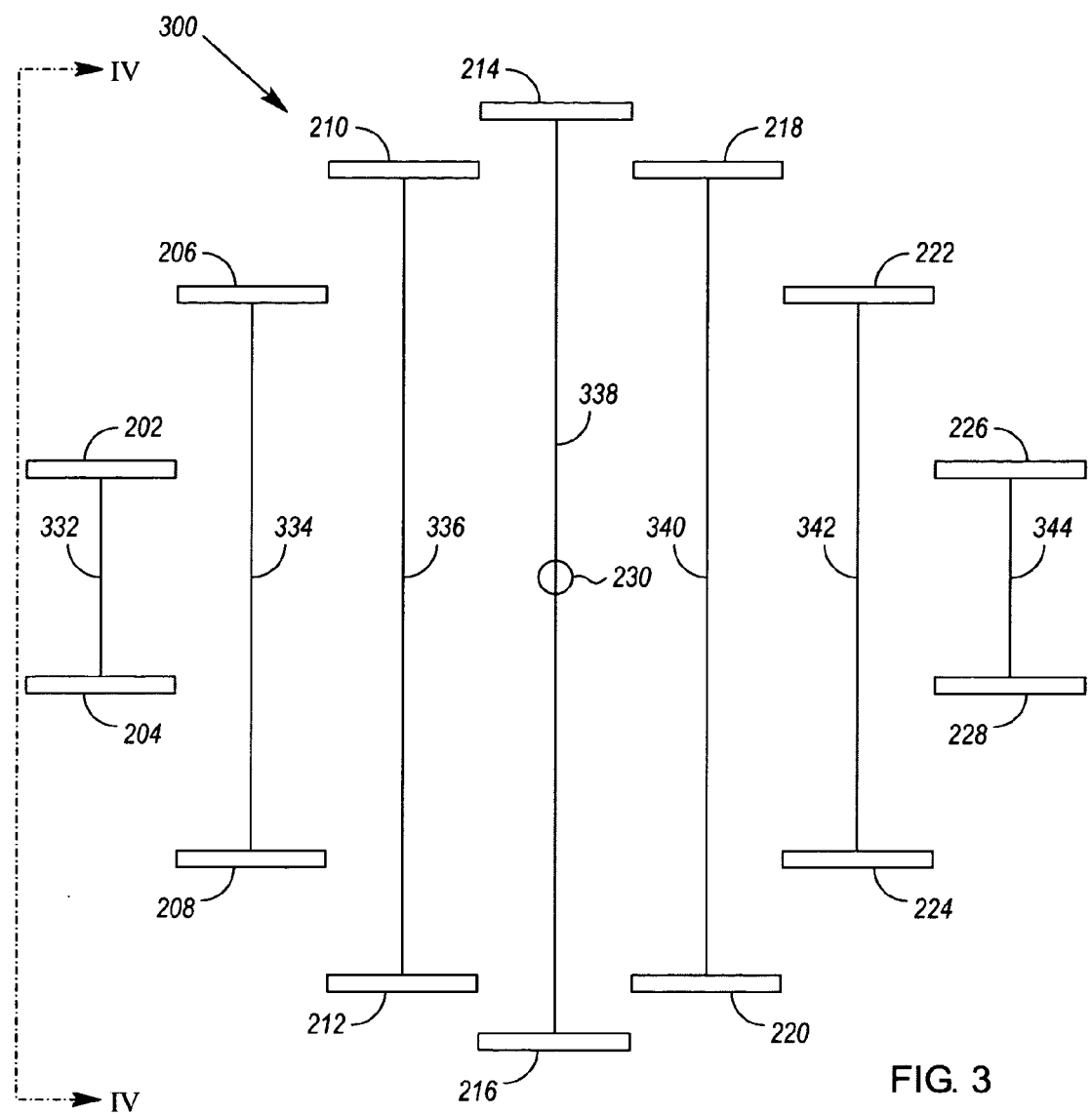
FIG. 3 illustrates the system design shown in FIG. 2 after relaxing the spacing of the detectors to provide for equally spaced scan passes over the detectors.
Figure 4:
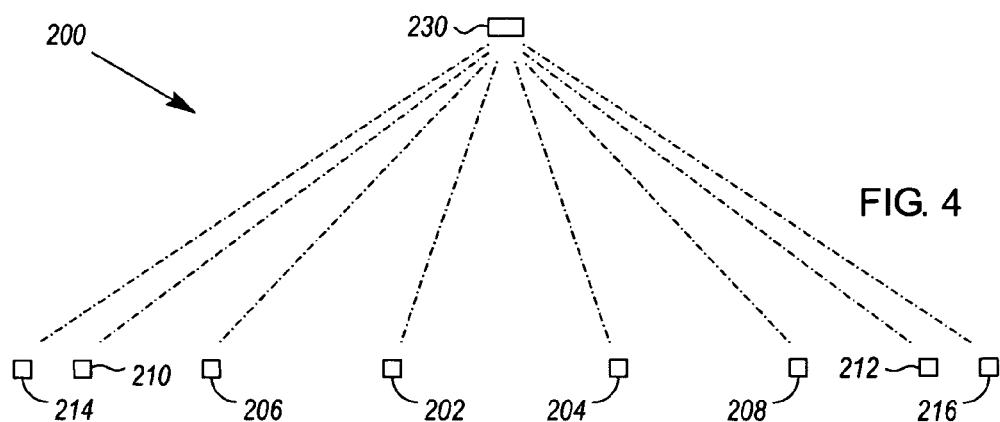
FIG. 4 illustrates an elevation of the system design shown in FIG. 3.

Note that the equally spaced azimuth angles of the design 200 result in unequal spacing between nominal scan passes 232–244. This unequal spacing can sometimes be undesirable. The system 300 shown in FIG. 3 therefore translates some of the detector pairs 206/208, 210/212, 218/220, 222/224 shown in FIG. 2 to provide a system design 300 with parallel nominal scan passes 332, 334, 336, 338, 340, 342, 344. It is noted that the nominal spacing between nominal scan passes is primarily a design tool. In actual operation of a radiographic system, it is possible and often desirable to deviate from nominal scan passes. To cite just one example, when the spacings between adjacent nominal scan passes are equal and correspond to the distance between adjacent detector centers, as illustrated in FIG. 3, then operating with a slightly smaller actual spacing between scan passes avoids potential problems at the boundaries of the detectors and guarantees that each point in a ROI will be imaged at least once by each detector.

Figure 5:
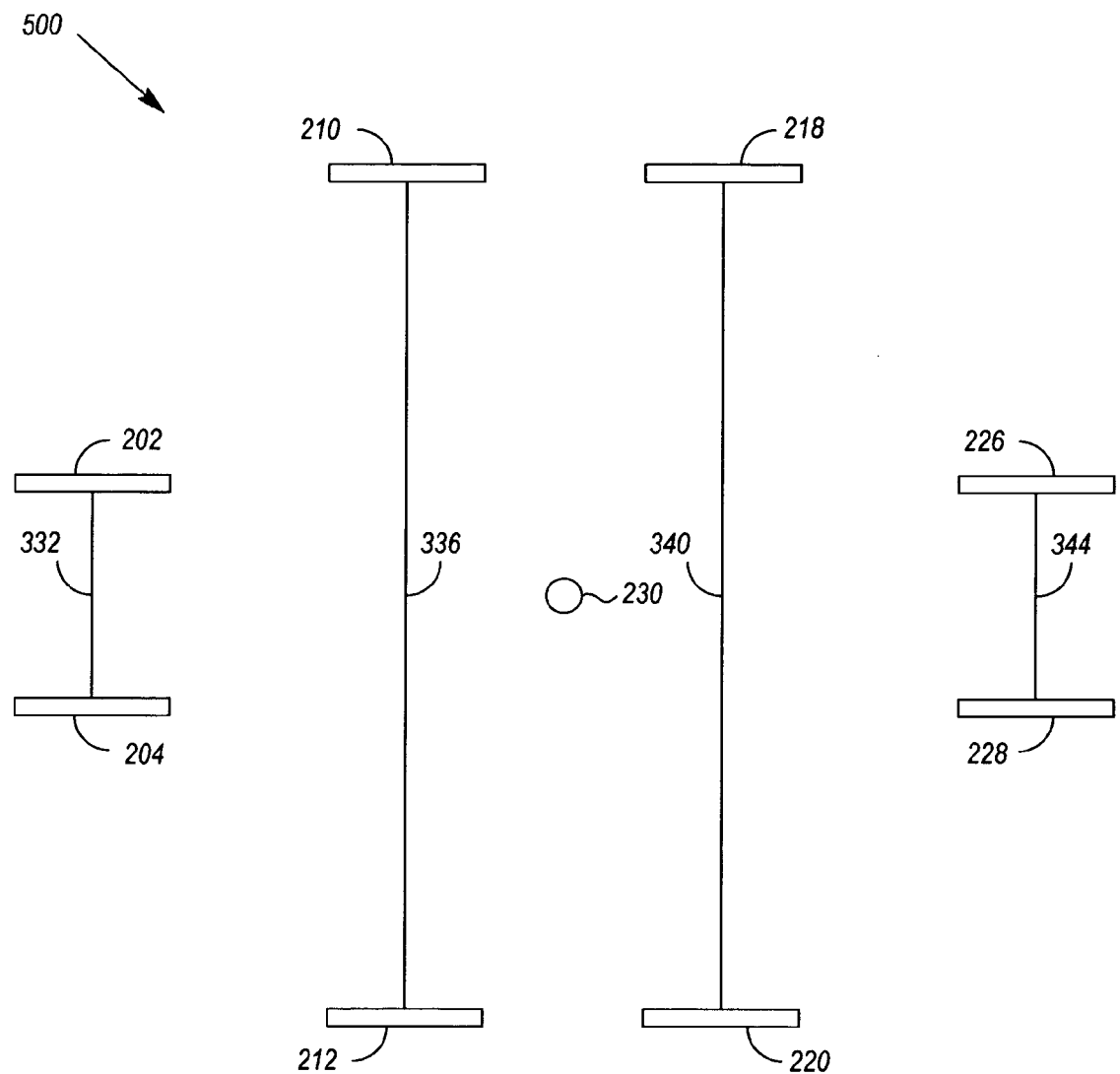
FIGS. 5 & 6 illustrate two exemplary subsets of detectors derived from the FIG. 3 system design.
Figure 6:
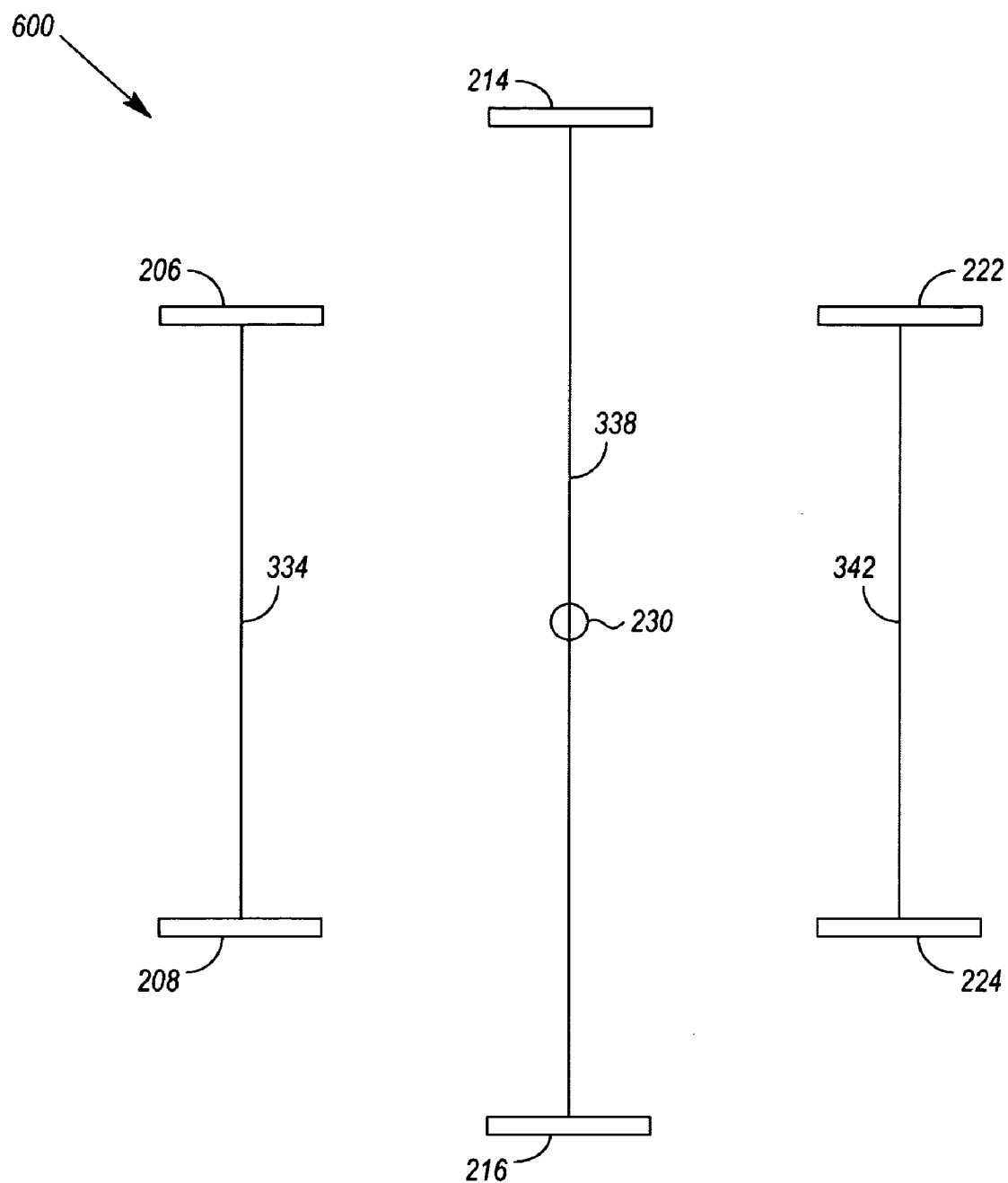

From the system design 300 shown in FIG. 3, a radiographic imaging system design 700 (FIG. 7) employing two radiographic sources 730a, 730b can be derived as follows. First, the detector pairs (i.e., the detectors corresponding to a common nominal scan pass) of the system design 300 having one source 230 may be divided into two sets 500, 600 by, for example, associating every other detector pair with a different set 500, 600. The resultant sets 500, 600 are shown in FIGS. 5 & 6. Note that each set 500, 600 of detectors maintains its same relationship with the radiographic source 230. Now consider that each set 500, 600 of detectors is associated with a replicated copy of the source 230 such that, during translation of one or both of the detector sets 500, 600 to cause an overlap of their nominal scan passes, the relationships between the radiographic detectors and source of a given set are maintained. That is, the detectors 706a, 708a, 714a, 716a, 722a and 724a in system design 700 have the same positions relative to source 730a as radiographic detectors 206, 208, 214, 216, 222 and 224 in system design 300 have relative to source 230; similarly, the detectors 702b, 704b, 710b, 712b, 718b, 720b, 726b and 728b in system design 700 have the same positions relative to source 730b as radiographic detectors 202, 204, 210, 212, 218, 220, 226 and 228 in system design 300 have relative to source 230.

In addition to requiring an additional radiographic source, the system design 700 utilizes a nominal spacing between scan passes that is twice that of the system design 300. The system design 700 therefore requires detectors 702b, 704b, 706a, 708a, 710b, 712b, 714a, 716a, 718b, 720b, 722a, 724a that are twice the length of the detectors 202–228 employed in the system design 300. Although the extra source and longer detectors increase the cost of the system design 700, note that the throughput of the system design 700 is roughly 1.75 times that of the system design 300, since it requires only four scan passes to image a specimen region of interest (as compared to the seven scan passes required by system design 300. (NOTE: The throughput is somewhat less than 1.75 times that of the system design 300 due to the increased lengths of some scan passes).

Figure 7:
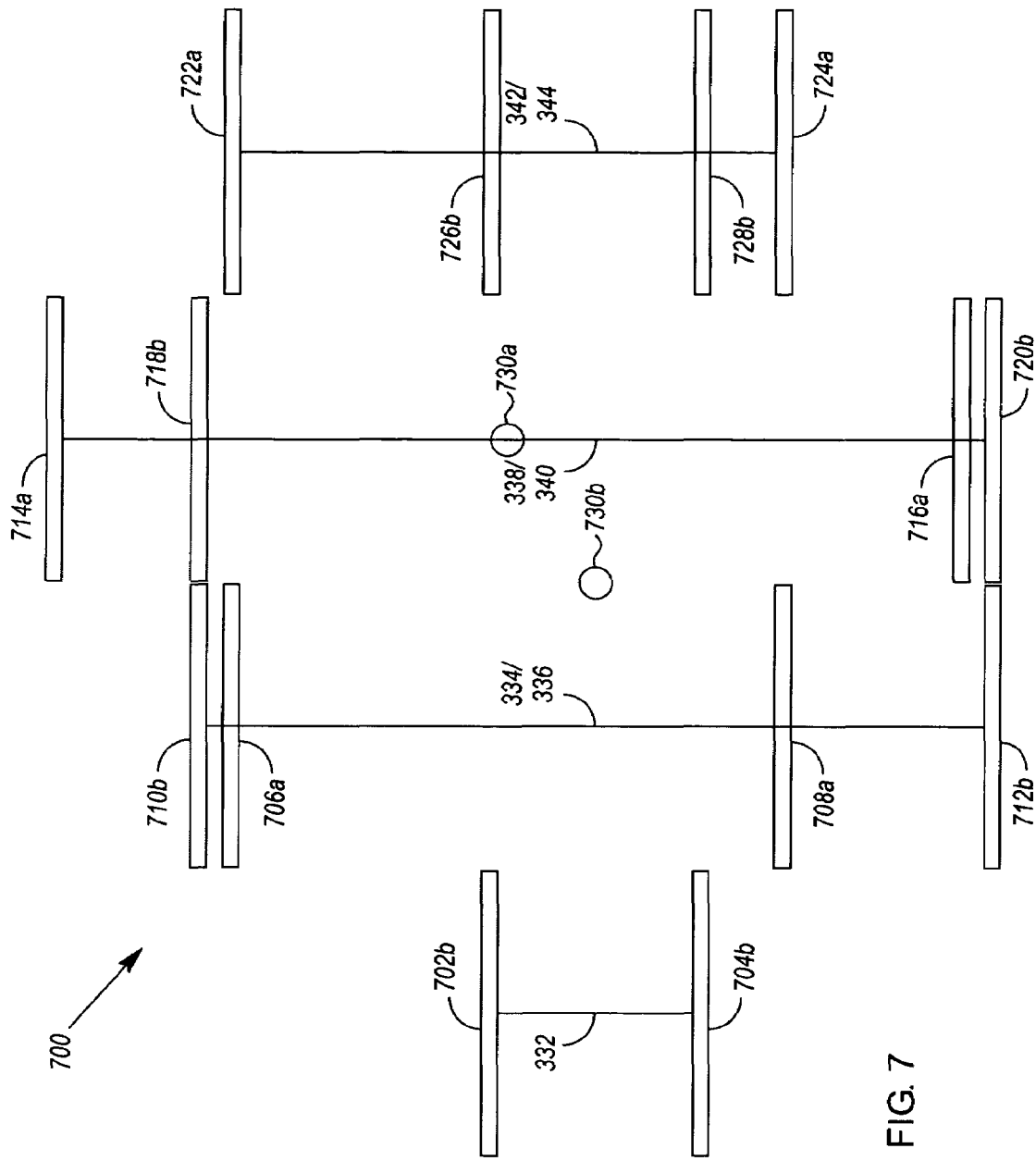
FIGS. 7–10 illustrate system designs based on the system design shown in FIG. 3, with each system design having a different number of radiographic sources and requiring a different number of scan passes.

One should note that the detectors 702b, 704b, 706a, 708a, 710b, 712b, 714a, 716a, 718b, 720b, 722a, 724a and sources 730a, 730b shown in FIG. 7 are not only horizontally translated, but also vertically translated (i.e., translated along the nominal scan passes). Although not required, vertical translation can be useful to adjust the distances between detectors or sources that are too close to one another (e.g., as a result of physical space requirements of the detectors or sources). Vertical translation can also be used to cause detectors from different sets to overlap or coincide. Overlapping detectors can then be eliminated, so long as the remaining detector can be configured to sense and distinguish the radiation emitted by different radiographic sources. The operation of such a dual-sensing detector will be described in more detail later in this description.

Figure 8:
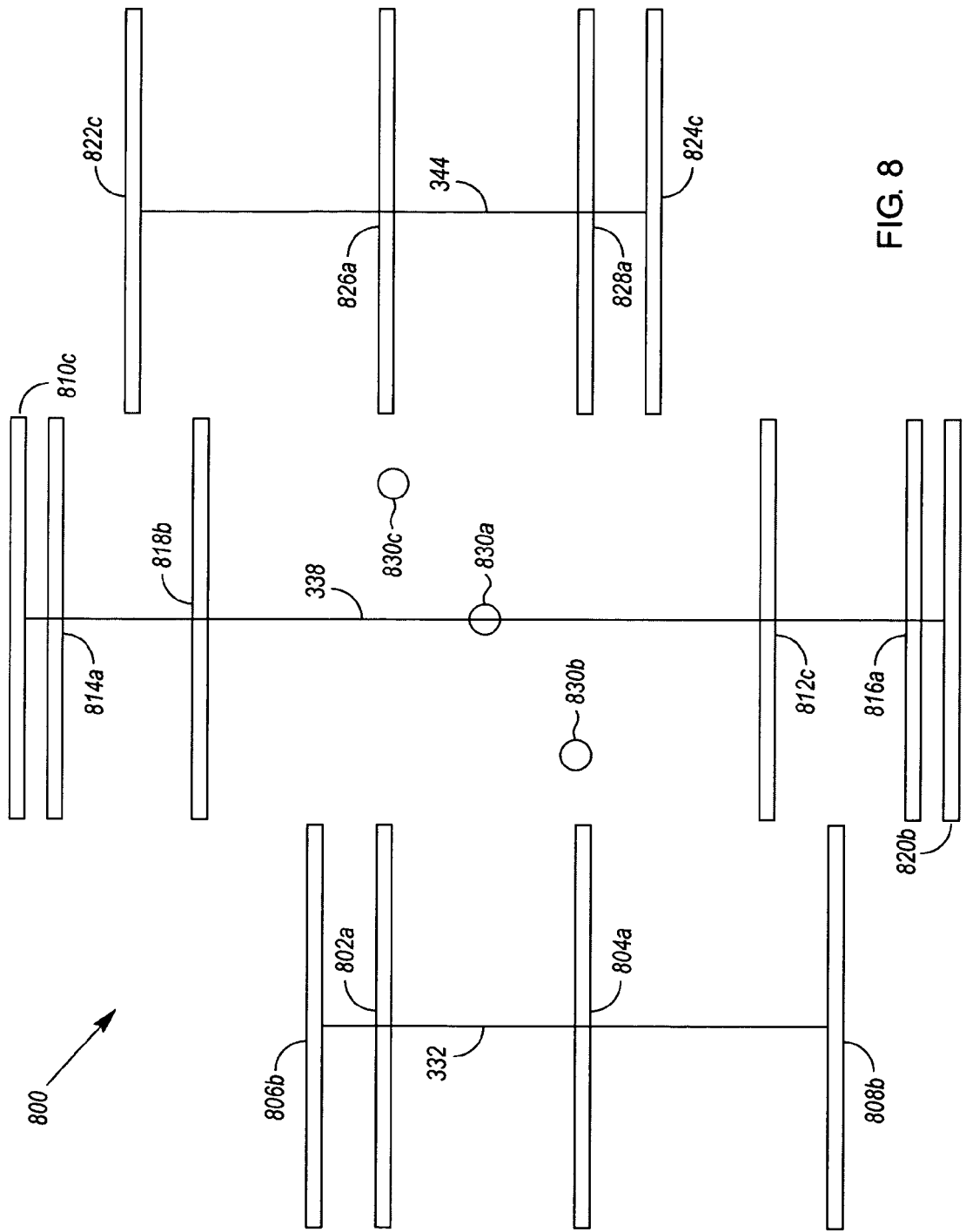
Figure 9:
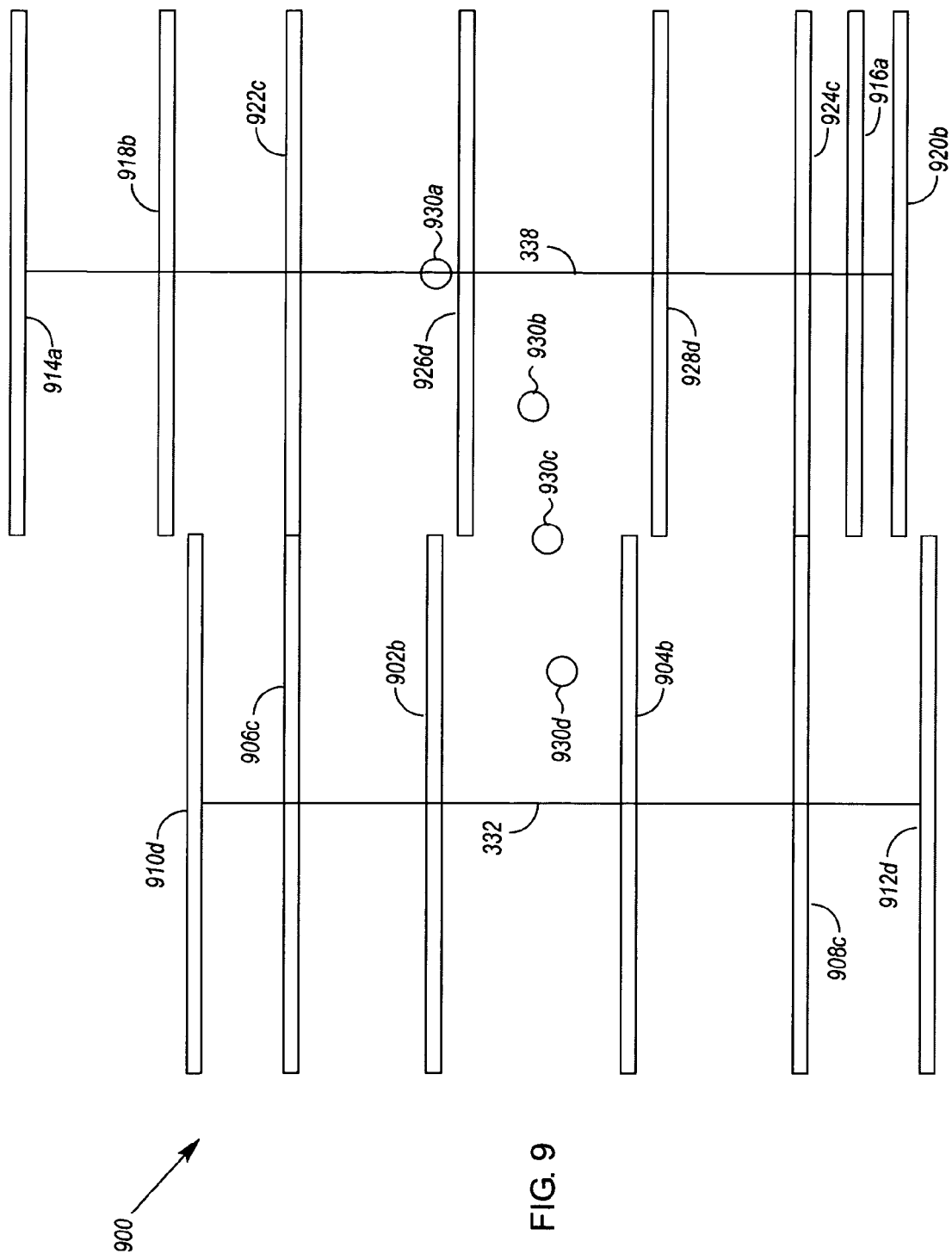
Figure 10:
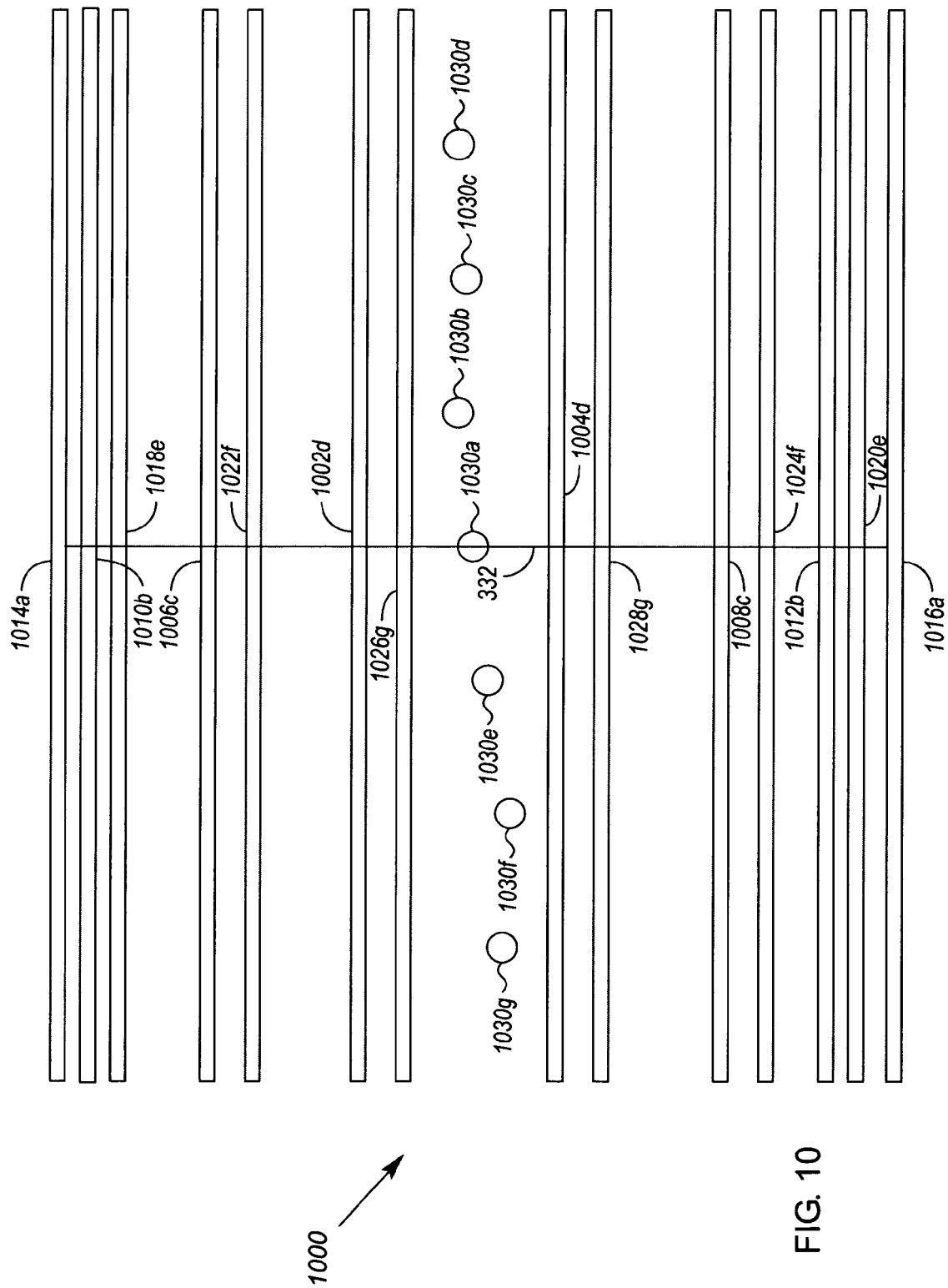

FIGS. 8–10 present three 830a, 830b, 830c, four 930a, 930b, 930c, 930d and seven source 1030a-g system designs 800, 900, 1000 based on the system design 300. In the system design 800, detectors 802a, 804a, 814a, 816a, 826a and 828a sense radiation emitted by source 830a; detectors 806b, 808b, 818b and 820b sense radiation emitted by source 830b; and detectors 810c, 812c, 822 and 824c sense radiation emitted by source 830c. In the system design 900, detectors 914a and 916a sense radiation emitted by source 930a; detectors 902b, 904b, 918b and 920b sense radiation emitted by source 930b; detectors 906c, 908c, 922c and 924c sense radiation emitted by source 930c; and detectors 910d, 912d, 926d and 928d sense radiation emitted by source 930d. In the system design 1000, detectors 1014a, 1016a sense radiation emitted by source 1030a; detectors 1010b, 1012b sense radiation emitted by source 1030b; detectors 1006c, 1008c sense radiation emitted by source 1030c; detectors 1002d, 1004d sense radiation emitted by source 1030d; detectors 1018e, 1020e sense radiation emitted by source 1030e; detectors 1022f, 1024f sense radiation emitted by source 1030f; and detectors 1026g, 1028g sense radiation emitted by source 1030g.

In each of the system designs 700, 800, 900, 1000, respectively, the detector pairs shown in the system design 300 are divided into an increasing number of detector sets, each of which is associated with a replication of the radiographic source 230 before being translated with respect to the other sets. The system design 300 therefore serves as a model on which the other system designs 700, 800, 900, 1000 are based. Alternately, one of the other system designs 700, 800, 900, 1000 could serve as a starting point, with sources being added or deleted, and detectors being translated, as desired. With system design 300 being the model, each of the system designs 700, 800, 900, 1000 are generated by translating one or more replicated sources and detector sets, thereby causing at least some of the nominal scan passes 332–344 in the system design 300 to coincide. It will be understood that system designs 700, 800, 900, and 1000 are exemplary rather than exhaustive, and many other equivalent designs can be generated using this method.

As a general rule, system designs 300, 700, 800, 900, and 1000 represent progressively more costly systems (due to their increasing number of sources and longer detectors) with greater throughput (due to their larger spacings between scan passes and corresponding reduction in the number of scan passes required). Each of these systems provides identical geometry and image quality when operated using nominal scan pass spacings. When operated with spacings other than nominal, the various systems designs, while no longer guaranteed to be identical, will nevertheless perform similarly.

Note that five and six source system designs based on the system design 300 are not shown. This is because these designs result in no further reduction in a system's required number of scan passes (i.e., there would be two required scan passes in four, five and six source designs, with a reduction to one scan pass not being possible until a seventh source is added).

By way of example, each of the system designs shown in FIGS. 3 & 7–10 shows a number of linear radiographic detectors having their long axes arranged in parallel and configured for use with linear scan passes. While convenient, and often desirable, these features are not essential. Thus, in alternate embodiments, the long axes of the detectors need not be parallel. Nor are the detectors required to be discrete or linear. For example, one or more area sensors could be used in place of one or more of the linear detectors, or the detectors could be curved rather than straight. Similarly, the scan passes could be curved rather than linear, so long as they are parallel.

The system designs shown in FIGS. 3 & 7–10 also illustrate a number of linear scan passes, with the nominal spacing between scan passes corresponding to the center-to-center spacing of groups of detectors arranged in columns. In alternate embodiments, the detectors need not be arranged in columns. Nor is it required that spacings between adjacent scan paths are all equal and correspond to detector center-to-center spacings. Detectors could also be arranged such that they intersect multiple scan paths. In yet other embodiments, scan passes could be curved rather than linear.

Figure 11:
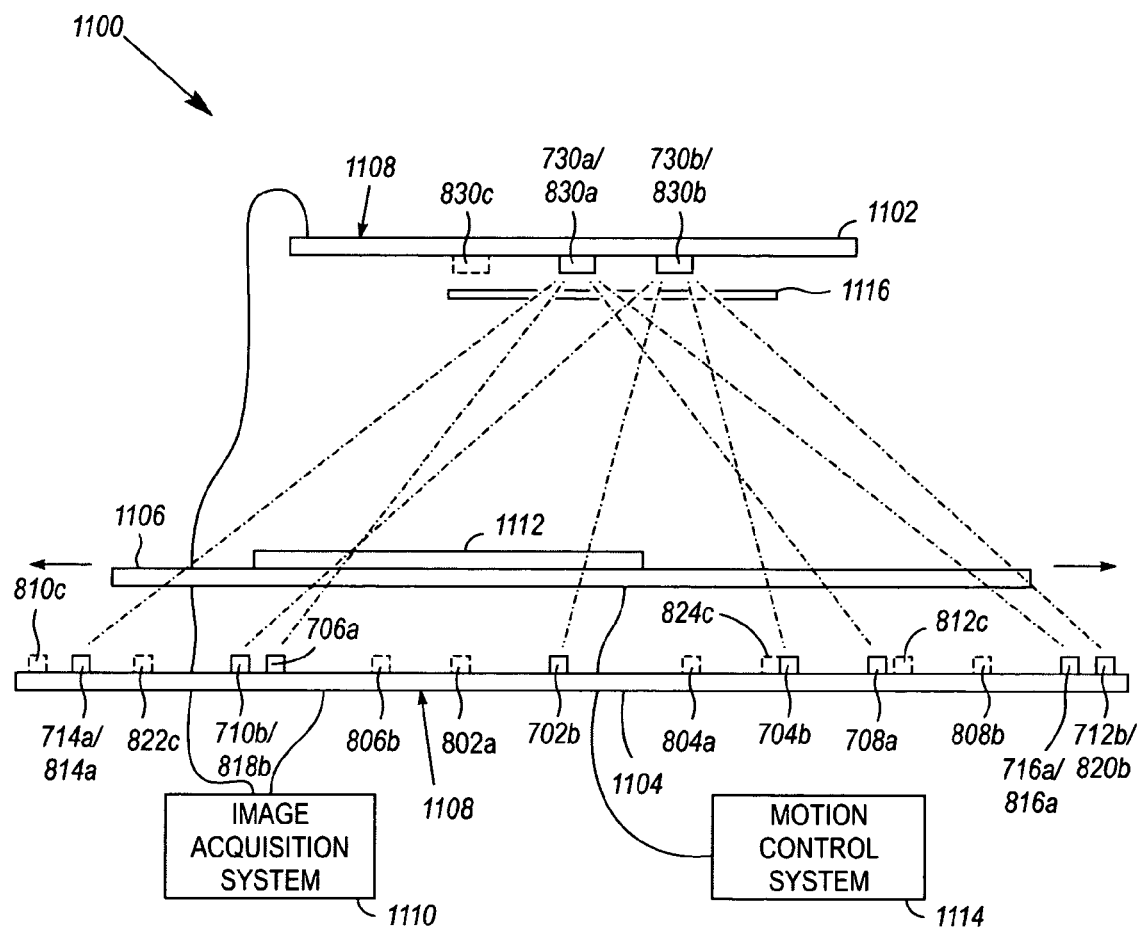
FIG. 11 illustrates a scalable radiographic imaging system platform.

FIG. 11 illustrates an elevation of some of the components of an exemplary scalable radiographic imaging system 1100 (e.g., an x-ray imaging or inspection system platform) that might implement one or more of the system designs shown in FIGS. 3 & 7–10. By way of example, the system 1100 is shown to be capable of implementing the system design 700 or the system design 800 (FIGS. 7 & 8). Alternately, the system 1100 could be modified to make it capable of implementing any of the system designs shown in FIGS. 3 & 7–10. Or, the system 1100 could be constructed in a non-scalable manner (e.g., by constructing it such that it only implements a single system design, such as system design 700).

The system 1100 comprises a first one or more structures (shown in FIG. 11 as one structure 1102) for holding a plurality of radiographic sources, and a second one or more structures 1104 (shown in FIG. 11 as one structure 1104) for holding a plurality of radiographic detectors. By way of example, the structures 1102, 1104 may comprise positions or elements (e.g., connectors, clips or brackets) for holding any of the source/detector combinations shown in FIGS. 7 & 8 (only some 810c, 714a/814a, 822c, 710b/818b, 706a, 806b, 802a, 702b, 804a, 824c, 704b, 708a, 812c, 808b, 716a/816a, 712b/820b of which are visible in the elevation shown in FIG. 11). Note that some radiographic sources and detectors (e.g., source 730a/830a and detector 714a/814a) are given plural reference numbers to indicate that one or the other of these detectors may be placed in these positions. Also note that some radiographic sources and detectors (e.g., source 830c and detector 810c) are shown with a dashed perimeter to indicate that these sources and detectors are not currently installed in the scalable system 1100.

As shown, the structures 1102, 1104 hold each radiographic source and its corresponding radiographic detectors in fixed positions with respect to each other, on opposite sides of a specimen holding platform 1106. By "fixed positions with respect to each other", it is meant that the sources and detectors are held in fixed positions with respect to each other during use of the system 1100. However, "fixed" does not mean that the sources and detectors are immovable. In one embodiment, the sources and detectors may be installed or removed from the system 1100 as necessary to implement either the system design 700 or the system design 800. In yet another embodiment, the individual detectors shown in FIG. 11 may be replaced with one or more area sensors, the surface(s) of which may be configured to simulate operation of the various detectors shown in FIG. 11.

Although the detectors included in the system 1100 are shown to lie in a common plane, they need not. In addition, the sources 830c, 730a/830a, 730b/830b could also lie in different planes, with different sources even being mounted on opposite sides of the specimen holding platform 1106. However, the placement of sources on opposite sides of the platform 1106 would also require the repositioning of detectors on opposite sides of the platform 1106. The sources and detectors of the system 1100 may, at times, be collectively referred to as an imaging system 1108.

The system 1100 further comprises an image acquisition system 1110. The image acquisition system 1110 operates the components of the imaging system 1108 as a specimen 1112 to be imaged moves relative to the imaging system 1108 (as will be described in the following paragraph).

A motion control system 1114 is used to vary the relative positions of the imaging system 1108 and the specimen holding platform 1106. In one embodiment, the motion control system 1114 may move the imaging system 1108 while the platform 1106 remains stationary. In an alternate embodiment, the motion control system 1114 may move the platform 1106 while the imaging system 1108 remains stationary. In yet another embodiment, the motion control system 1114 may move both the imaging system 1108 and the platform 1106. Not only does the motion control system 1114 move the specimen holding platform 1106 in a number of scan passes in relation to the system's detectors, but depending on the system design for which the system 1100 is currently configured, the motion control system 1114 may also translate the platform 1106 or imaging system 1108, between scan passes. At least some of the scan passes cause radiation from at least two of the radiographic sources 730a/830a, 730b/830b to be 1) transmitted through a specimen region of interest, and 2) detected by radiographic detection areas 706a, 708a, 714a, 716a, 722a, 724a, 702b, 704b, 710b, 712b, 718b, 720b, 726b, 728b belonging to at least two corresponding sets of radiographic detection areas.

When multiple radiographic sources (e.g., source 730a, 730b) are installed in the imaging system 1108, different sets of the detectors may need to be configured to sense radiation transmitted by different ones of the sources. For example, the source 730b may need to illuminate only detectors 702b, 704b, 710b, 712b, 718b, 720b, 726b and 728b.

In one embodiment of the system 1100, a mechanical radiographic collimation system 1116 is used to collimate and direct the radiation emitted by each source 830c, 730a/830a, 730b/830b toward its corresponding detectors. As shown, the collimation system 1116 may comprise a plurality of apertures that restrict which sources illuminate which detectors. The collimation system 1116 may be positioned nearer to the source(s), as shown, or nearer the detectors, in which case the positions of the collimation system's apertures would be adjusted accordingly. Combinations of source and detector collimation can also be used. Alternately, the image acquisition system 1110 may operate corresponding ones of the radiographic sources and detectors in a time-division multiplexed manner. In this manner, mechanical collimation can be eliminated or reduced, since only one source is energized at a time, and radiation readings are only acquired from a detector when its corresponding source is energized.

Another way to eliminate or reduce the need for a mechanical radiographic collimation system 1116 is to modulate the radiographic sources using unique, orthogonal modulation sequences. In this manner, all of the sources and detectors can be operated in parallel, and an appropriate one of the modulation sequences can be applied to the data acquired from a given detector to derive the component of radiation received from the detector's corresponding source. Due to the orthogonal nature of the modulation sequences, all other radiation received by a detector can be treated as noise, and factored out of its radiation readings.

Yet another way to eliminate or reduce the need for a mechanical radiographic collimation system 1116 is to configure (or select) each radiographic source to emit a different wavelength of radiation. The detectors corresponding to a particular source can then be filtered so that they only detect the radiation emitted by their corresponding source. If wavelength sensing detectors rather than filters are used, overlapping detectors from different groups can be combined, as described previously.

One of ordinary skill in the art, after reviewing the above paragraphs, will understand that the methods described herein for ensuring that each detector is only responsive to radiation from a corresponding source(s) are not mutually exclusive. Nor are they exhaustive.

In one embodiment, the system 1100 may be provided with 12–16 linear radiographic detectors, and even more preferably, fourteen radiographic detectors. However, the system 1100 may alternately be provided with more or fewer detectors. As previously mentioned, an area sensor may In some cases, the detectors may be time-domain integration detectors.

What is claimed is:

1. A method for generating alternative radiographic imaging system designs, comprising:
  receiving a number of design constraints for a radiographic imaging system; and
  in response to the constraints, generating the alternative radiographic imaging system designs, each having a different number of radiographic sources, and each requiring a different number of nominal scan passes to image a specimen region of interest; wherein radiographic imaging system designs having a greater number of radiographic sources comprise sets of translated radiographic detection areas sharing at least some coincident, nominal scan passes as compared to radiographic imaging system designs having fewer radiographic sources, with each set of translated radiographic detection areas being associated with a radiographic source that is replicated and translated with respect to a radiographic source that forms part of a radiographic imaging system design having fewer radiographic sources.

2. The method of claim 1, wherein the radiographic detection areas are linear detection areas, and wherein a radiographic imaging system design having a greater number of radiographic sources is provided with longer linear detection areas than a radiographic imaging system design having a fewer number of radiographic sources.

3. The method of claim 1, wherein the design constraints comprise one or more constraints pertaining to system image quality.

4. The method of claim 1, wherein at least one of the design constraints is selected from a group consisting of: system image quality, system cost, and system throughput.

5. The method of claim 1, further comprising, for multiple radiographic source system designs, translating positions of some radiographic sources and their corresponding radiographic detection areas along the nominal scan passes to adjust distances between the radiographic detection areas.

6. The method of claim 1, further comprising, for multiple radiographic source system designs,
  translating positions of some radiographic sources and their corresponding radiographic detection areas along the nominal scan passes, until radiographic detection areas corresponding to different radiographic sources overlap; and
  eliminating one of the overlapping radiographic detection areas, thereby enabling the use of one radiographic detection area to sense radiation emitted by different radiographic sources.

7. The method of claim 1, further comprising, associating each of said radiographic imaging system designs with one or more design characteristics that were not specified as design constraints prior to generating said plurality of radiographic imaging system designs.

* * * * *